(12) United States Patent
Basara

(10) Patent No.: US 6,596,299 B1
(45) Date of Patent: Jul. 22, 2003

(54) METHOD OF TREATING PERIODONTAL DISEASE

(75) Inventor: Michael Basara, Hugo, MN (US)

(73) Assignee: Northern Research Laboratories, Inc., Minneapolis, MN (US)

(*) Notice: Subject to any disclaimer, the term of this patent is extended or adjusted under 35 U.S.C. 154(b) by 0 days.

(21) Appl. No.: 09/575,297

(22) Filed: May 19, 2000

(51) Int. Cl.[7] ............... A61K 6/00; A61K 9/08; A61K 7/16
(52) U.S. Cl. ............ 424/435; 424/400; 424/422; 424/434
(58) Field of Search .............. 424/422, 49, 400, 424/434, 435

(56) References Cited

U.S. PATENT DOCUMENTS

| | | | |
|---|---|---|---|
| 4,080,212 A | * | 3/1978 | Takahashi ............... 106/35 |
| 4,599,228 A | * | 7/1986 | Ladanyi ................. 424/52 |
| 5,566,828 A | * | 10/1996 | Claes et al. ............ 206/570 |
| 5,898,037 A | * | 4/1999 | Marx .................... 424/49 |

OTHER PUBLICATIONS

Peckham et al. Periodontal Disease, Nidus Information Services, Inc. Mar. 1999.*
Northern Research Laboratories, Debacterol Trademark Registration, Jul. 1996.*
Northern Research Laboratoreies, Debacterol Overview, Last Modified: Jan. 17, 2002.*

* cited by examiner

*Primary Examiner*—Thurman K. Page
*Assistant Examiner*—Rachel M. Bennett

(57) ABSTRACT

The present invention includes a method for treating periodontal disease. The method comprises delivering to a pocket of a tooth with periodontal disease, a viscous, reddish-brown solution comprising sulfuric acid and sulphonated phenolic compounds. The method also comprises retaining the reddish-brown solution in the pocket for t time ranging from about 5 seconds to about 60 seconds.

10 Claims, 6 Drawing Sheets

METHOD OF TREATING PERIODONTAL DISEASE

BACKGROUND OF THE INVENTION

The present invention relates to a method for treating periodontal disease.

Periodontal disease is characterized by a loss of supporting tissues of the teeth. In particular, periodontitis includes a loss of the periodontal ligament and a disruption of the ligament attachments to cementum, as well as reabsorption of alveola and bone. Along with a loss of tissue attachments, periodontal disease produces a migration of the epithelial attachments along the root surface and reabsorption of bone.

It is widely accepted that an initiation and progression of periodontal disease is dependent upon the presence of micro-organisms which are capable of causing the disease. At least three characteristics of periodontal micro-organisms have been identified which contribute to the ability of microbes to act as pathogens. A first characteristic is a capacity of the microbes to colonize. A second characteristic is an ability of the microbes to evade anti-bacterial host defense mechanisms. A third characteristic is an ability of the microbes to produce substances which directly initiate tissue destruction.

Two major periodontal disease pathogens, *A. actinomycetemcomitans* and *P. gingivalis*, are able to invade into the tissues. *A. actinomycetemcomitans* passes through epithelial cells into the underlying connective tissue while *P. gingivalis* invades and persists in epithelial cells.

It is believed that direct pathological effects of bacteria and effects of their products on the periodontium are significant during early stages of periodontal disease. Analysis of plaque samples from patients with increasingly severe levels of gingival inflammation reveals a succession of bacterial species with an increased capacity to directly induce an inflammatory response. For example, an increase in persistent levels of *Fusobacterium nucleatum* incites a mild gingivitis. A subsequent production of its metabolic by-products directly effects gingival vasculature. Resulting edema and an increase in production of, gingival crevicular fluid, GCF, provides an environment and nutrients that allow putative pathogens to flourish.

Bacteria such as *P. gingivalis* also produce enzymes such as proviasis, collagenase, and fibrinolysin that directly degrade surrounding tissues in superficial layers of the periodontium. In addition, this bacterium produces metabolic by-products such as $H_2S$, ammonia and fatty acids that are toxic to surrounding cells. Furthermore, bacterial constituents such as lipopolysaccharide are capable of inducing bone reabsorption in vitro.

Once major protective elements of the periodontium have been overwhelmed by bacterial virulence mechanisms, several host-mediated destructive processes are initiated. Polymorphonucleocytes (PMNS), which normally provide protection can themselves contribute to tissue pathology. During a process of phagocytosis, PMNs typically spill some of the enzyme content extracellularly during a process known as degranulation. Some of the enzymes are capable of degrading the surrounding host tissues, such as collagen and basement membrane constituents, which contribute to tissue damage.

There is increasing evidence that the bulk of tissue destruction in established dental lesions is a result of the mobilization of the host tissues by an activation of monocytes, lymphocytes, and other host cells. Engagement of these cellular elements by bacterial factors, in particular bacterial lipopolysaccharide, is thought to stimulate production of both catabolic cytokines and inflammatory mediators such as arachidonic acid and metabolites, such as prostaglandin $E_2$ ($PGE_2$). Such cytokines and inflammatory mediators, in turn, promote the release of tissue-derived enzymes. A summary of this reaction is described in an article, "The Pathogenesis of Periodontal Diseases", *Periodontal*, April 1999, Vol. 70, No. 4, pp. 457–470.

In some aspects, periodontal diseases are among the most unusual infections of human beings. One reason for this uniqueness is the unusual anatomic feature wherein a mineralized structure, a tooth, passes through an integument so that a portion of the tooth is exposed to an external environment while a portion is within connected tissues. This unusual aspect of the infection is described in an article entitled "The Nature of Periodontal Diseases" by S. Socransky et al. in *The Annals of Periodontology*, vol.2, No. Mar. 1, 1997, pp. 4–10.

The tooth provides a surface for colonization by a diverse array of bacterial species. Bacteria attach to the tooth itself as well as to the epithelial surface of the gingival or periodontal pockets, and to underlying connective tissues. The outer layers of the tooth do not shed, and thus microbial colonization is facilitated. A situation is then established wherein micro-organisms colonize a relatively stable surface, which is the surface of the tooth, and are continually held in immediate proximity to soft tissues of the periodontium.

The presence of the tooth increases the complexity of the host-parasite relationship in a number of ways. The bacteria colonizing the tooth are by and large outside the body where they are less able to be controlled by mechanisms which operate within the tissues. The environment within a plaque is conducive to microbial survival, but it is unlikely to be particularly an effective environment for a host to seek out and destroy micro-organisms.

Factors such as pH, eH and proteolytic enzymes affect performance of host defense mechanisms. In addition, the tooth provides sanctuary in which micro-organisms hide, persist at low levels during treatment, and then re-emerge to cause further problems. Bacteria in dentin alluvials, which are flaws in the tooth, or areas which were demineralized by bacteria, are not easily approached by much larger host cells. In a similar manner, non-cellular host factors face diffusion barriers. Mechanical debridement, other than vigorous removal of tooth material, cannot reach organisms in the tooth. Chemotherapeutic agents also have difficulty in reaching the bacterial species. In particular, antimicrobial agents which require bacteria to multiply are adversely affected since the rate of growth is suspected to be very low.

One method for measuring the severity of periodontal disease is a technique of periodontal probing depth (PD). Measuring periodontal probing depth measures a loss of connective tissue attachments. A method of periodontal probing has been described in an article entitled "Periodontal Probing: Probe-tip Diameter*", published by the School of Dentistry, Medical College of Georgia, Augusta, Ga.

Periodontal probing is performed when a periodontist places a probe into the sulcus or clinical pocket, and applies a force to move it apically into tissue along a tooth surface. The clinician applies pressure on the tissue and when the tissue exerts an opposite, equal pressure to the probe, displacement of the probe into the tissue will cease. The pressure exerted by the probe is directly proportional to force on the probe and inversely proportional to the area at the probe tip. With a round probe, a change in the tip diameter has a greater effect on pressure than does a similar change in the force. An increase in the probing force increases the pressure by a proportional amount. However, a relatively similar increase of the probe diameter reduces the pressure by a proportional amount which is squared. If the force is doubled (20 to 40 gramforce), the pressure is increased by a factor of 2. If the diameter is doubled (0.4 to 0.8 millimeters), the pressure is reduced by a factor of 4. The pressure is equal to the force applied in the probe/area at the tip-end=$F/ur^2$=$F/u(D/2)^2$: R=radius, D=diameter.

Positioning of the probe is shown in schematic cross-section in FIG. 1. The probe 10 is inserted in an area between connective tissue 12 and dentin 14, as is shown in FIG. 1. The depth 16 of the probe 10 into that space is a measure of the severity of periodontal disease.

In early periodontitis, gums appear similar to those in gingivitis. However, the seal around a tooth has been destroyed and the bone is starting to eat itself away. This is an attempt by the body to escape advancing bacterial invasion. At this time, pockets are 4 to 5 millimeters deep.

In moderate periodontitis, the infection has eaten away more bone. Gums are receding, exposing root surfaces. Pus may be present. Pockets are up to about six millimeters deep. At this state of infection, the infection may still be treated non-surgically. However, once the bone is lost, it does not grow back. The teeth are weakened by partial loss of the supporting bone. In advanced periodontitis, bone loss becomes more severe. The gum tissue has now become more like scar tissue. The scar tissue must be cut out surgically to get ride of the pockets. Advanced periodontal pockets usually measure more than 6 millimeters.

Treatment regimens for periodontal disease typically involve removal of mechanical irritants, such as plague and calculus, and removal of as many bacteria as possible. The tissues are made as cleansable and as healthy as possible. The patient is taught to keep teeth and gums clean. Non-surgical treatment includes scaling and root cleaning, which is deep root cleaning of teeth to physically remove all tartar and plaque. The teeth are polished to remove stains and to make the teeth harder for the plaque to adhere to. Prescription and non-prescription medications are applied to the gums. Mouth rinses are used in conjunction with improved home care. Antibiotics are sometimes used.

Kakwarf et al., in an article entitled "Cytologic Evaluation of Gingival Curettage Facilitated by a Sodiumhypochloride Solution", *Internal Periodontology*, February 1992, pp. 63–69, describes a use of an instrument against a gingival side of a pocket, in order to scrape and debride soft tissue. The purpose of this scraping and debriding is to remove inflamed tissue and to maintain teeth and gums in a state of periodontal health. In some treatments, sodium hypochlorite solution was introduced along with the curettage in order to remove all the epithelium from a pocket. Citric acid treatment has also been used to augment epithelial treatment.

Local controlled delivery of antibiotics has also been performed in conjunction with scaling and root cleaning. One antibiotic delivered through a controlled release mechanism is doxycycline hyclate. This type of treatment was described in an article written by Garret et al., entitled "The Effect of Locally-delivered Controlled Release Dioxycycline on Scaling and Root Cleaning on Periodontal Maintenance Patients over Nine Months", *Periodontal Period*, Vol. 71, No. 1 January 1, 2000, pp. 2–9. Other antibiotics delivered through this type of format include the tetracycline.

In cases of advanced periodontal disease, the gum adjacent to the diseased tooth is lifted from the tooth and bone, and diseased tissue is removed. The infected bone may also be reshaped. After surgery, the gum is repositioned and sutured into place.

In some cases, destroyed tissue between teeth or roots is partially regenerated. Once damaged area of tissue is removed and special membranes are inserted, new tissue grows over a period of weeks to months. This type of regeneration, as measured by a probe test, typically results in a decrease in probe depth of only about 1 millimeter.

SUMMARY OF THE INVENTION

One embodiment of the present invention includes a method for treating periodontal disease. The method comprises delivering to a pocket of a tooth with periodontal disease, a viscous, reddish-brown solution comprising sulfuric acid and sulphonated phenolic compounds. The method also includes retaining the reddish-brown solution in the pocket for a time ranging from about 5 seconds to about 60 seconds.

Another embodiment of the present invention includes a method for saving condemned teeth. The method comprises delivering to a pocket of a tooth with periodontal disease, a viscous, reddish-brown solution comprising sulfuric acid and sulphonated phenolic compounds. The method also includes retaining the reddish-brown solution in the pocket for a time ranging from about 5 seconds to about 60 seconds.

One other embodiment of the present invention includes a needle for delivering a treatment solution for periodontal disease. The needle comprises a deformable main body that defines a side hole for delivery of the treatment solution.

Another embodiment of the present invention includes a kit for treating periodontal disease. The kit comprises a container with a treatment solution comprising a viscous, reddish-brown solution comprising sulfuric acid and sulphonated phenolic compounds. The kit also comprises a needle for delivering the treatment solution to a pocket of a diseased tooth.

DETAILED DESCRIPTION

Figure 2:
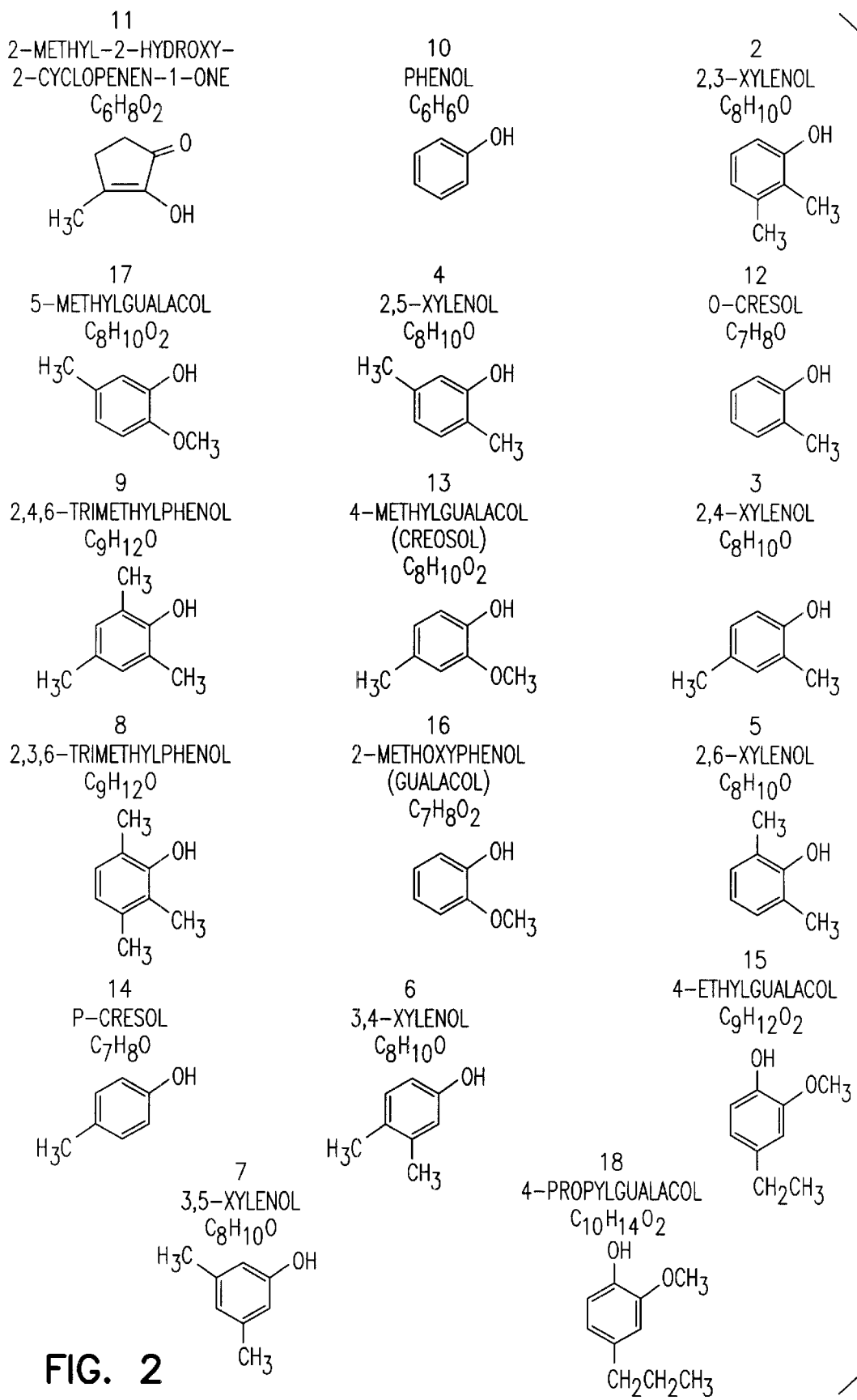
FIG. 2 is a view of the components of the treatment solution of the present invention.

One method aspect of the present invention includes a method for treating periodontal disease. The method comprises providing a syringe, with a needle, such as is shown at 30 in FIG. 3 and providing a reddish-brown, sulphonated phenolic solution, ingredients of which are shown in FIG. 2. The method includes performing a conventional scale and planing treatment. Scaling removes calculus and plaque on a tooth. Planing is a rubbing against the root of the tooth, such as is shown at 40 in FIG. 4. Next, using a syringe and syringe needle of the present invention 30, water is delivered to a pocket 42 of the scaled and planed tooth. Water is added until the water is expressed at least one portion of a circumferential interface 44 where the gum meets the tooth 40. Expressed water is removed from the patient's mouth by suction.

A second syringe is loaded with the reddish-brown, sulphonated phenolic solution. The needle of the present invention 30 is installed on the syringe. The needle is inserted into the pocket of the tooth and the reddish-brown, sulphonated phenolic solution is delivered to the pocket.

The sulphonated phenolic solution is added until the solution is expressed in about the same location as the water had been expressed. The sulphonated phenolic solution is retained in the pocket 42 for a period of time ranging from about 10 seconds to about 60 seconds. Suction is then applied at the point of expression in order to remove the sulphonated phenolic solution. Water is then added to the pocket in order to rinse any remaining sulphonated phenolic solution from the pocket. The water is added until liquid expressed is clear. Expressed liquid is removed by suction.

For some method embodiments, high pressure water is then added to the pocket 42. The high pressure water irrigates the pocket 42 and removes all necrotic debris from within the infected area. Antibiotic treatment, typically employed in treatment of periodontal disease, is not necessary with the method of the present invention.

It has surprisingly been found that the method of the present invention not only substantially eliminates pain associated with periodontal disease, but appears to reverse tissue damage and destruction caused by etiological agents of periodontal disease. In particular, it has been observed that following treatment with the method of the present invention, even teeth such as condemned teeth, are salvageable. This is a heretofore unobserved phenomenon. It is even more surprising that these remarkable results are achievable without a use of antibiotics.

It is not understood exactly how the method of the present invention is able to initiate tissue regeneration. It is believed that the ability of the sulphonated phenolic compound to remove necrotic and other diseased tissue while preserving healthy tissue at the interface is responsible for rapid tissue regeneration. It is not known whether tissue regeneration includes regeneration of the ligament or surrounding mucosal tissue or both. It has been observed, however, that probe depth is decreased by a length of up to about 5 millimeters following treatment! Successful treatments using regimens described herein, such as time release of antibiotics, have been regarded as successful if probe depth reduction was about 1 millimeter. No method of periodontal treatment heretofore known has been able to salvage condemned teeth, as is the case with the method of the present invention.

One other benefit of the method of the present invention is that it is a single treatment-based method. It is not necessary to install an appliance which engages in continuous release of drugs. After the single treatment, remaining tissue is in a condition wherein it is able to regenerate on its own. Because of the rapidity of regeneration and the health of the surrounding and remaining tissue, bacterial reinfection does not occur, provided the patient engages in good oral hygiene. Consequently, follow up antibiotic treatment is not necessary.

As used herein, the viscous, sulphonated phenolic compound refers to Debacterol, a mixture of 50% sulfuric acid, 4% sulfonated phenol and 24% sulfonated phenolics, including guaiacol, resol, creosol and xylenol in an aqueous solution, which is manufactured by Northern Research Laboratories, Inc., of 8400 Normandale Lake Blvd., Suite 920, of Minneapolis Minn. 55437-1085. The viscous, sulphonated phenolic compound comprises the following ingredients in the following concentrations:

| Sulphonated Compound Group | Weight % |
| --- | --- |
| Phenol | 2.5 to 7.5 |
| Cresols | 5 to 7.5 |
| Creosols | 5 to 15 |
| Xylenol | 5 to 7.5 |
| Guaiacol | 5 to 15 |

One specific embodiment had the following concentration ranges:

| Sulphonated Compound Group | Weight % |
| --- | --- |
| Phenol | 3.10 to 4.94 |
| Guaiacol | 9.14 to 14.56 |
| Cresol | 3.49 to 5.56 |
| Creosol | 3.81 to 6.07 |
| Xylenol | 4.52 to 7.21 |
| Total | 24.06 to 38.34 |

Figure 1:
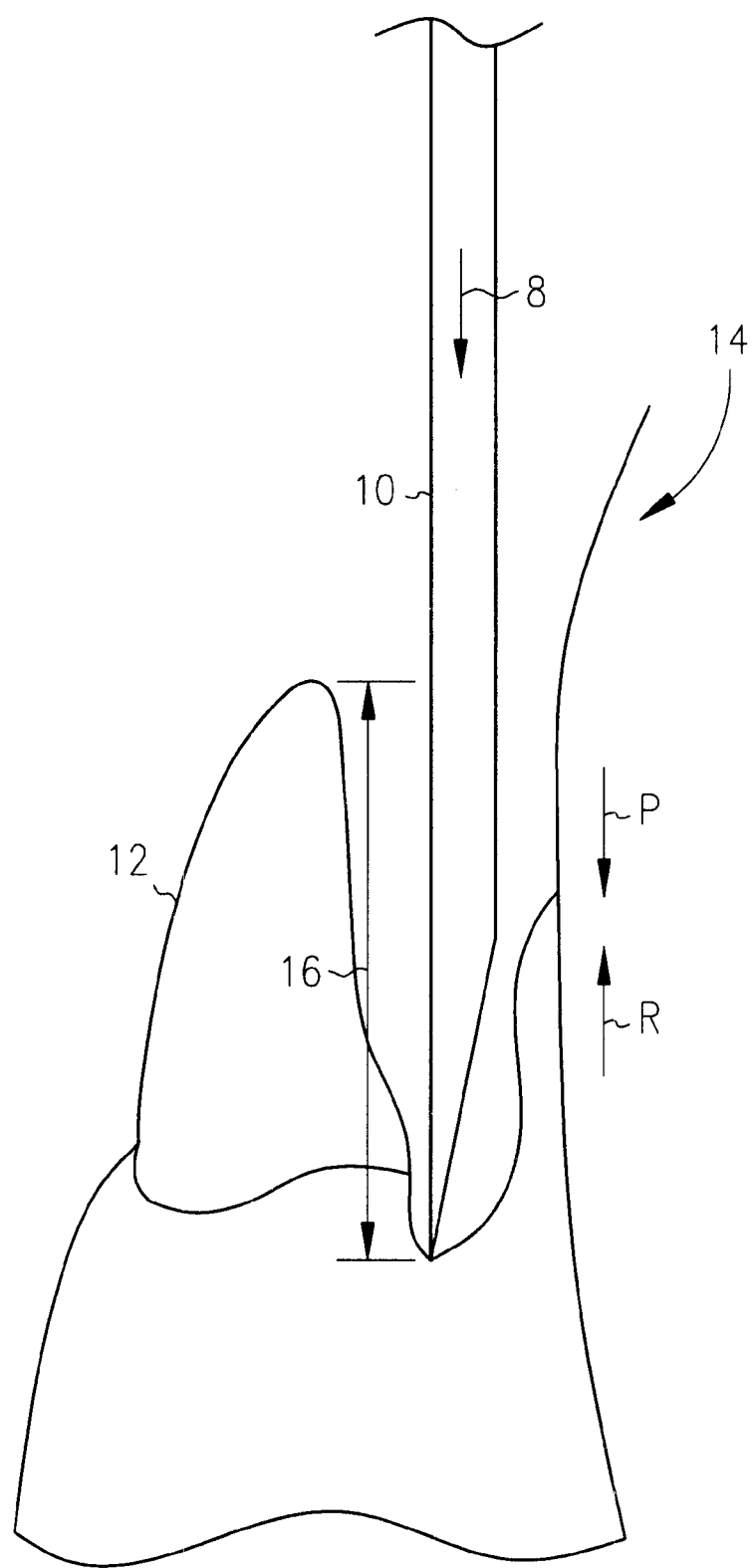
FIG. 1 illustrates a cross-sectional view of one embodiment of a probed tooth with periodontal disease.

A breakdown of phenolic compounds in this aqueous solution is shown in FIG. 1. The source of the Debacterol phenolic components is beechwood creosote. The Debacterol solution has a dark reddish-brown color that renders the material visible when applied to the lesion and surrounding healthy tissue. Specific phenolic components include sulfonated phenol, 4-methoxyphenol (Gualacol), 3,4-xylenol, and o-cresol.

The Debacterol density is 1.08 gms per ml at 20 degrees Centigrade. The distillation range is 200 to 230. The flash point is about 99 degrees Centigrade. Debacterol has a percent moisture of about 10 to 19%, an acidity as (mg/kg) calcium carbonate of 480,000 to 487,000 and a percent 4-OH benzene sulfonic acid, wt./wt. of 3.2 to 4.5.

As used herein, "condemned teeth" refers to teeth associated with such severe periodontal disease that the teeth are regarded as not capable of being saved. Condemned teeth are typically extracted.

As used herein "probe depth" refers to a measurement of a loss of connective tissue attachments. In early gingivitis, probe depth is about 4 to 5 millimeters. With moderate periodontitis, probe depth is about 6 millimeters. For advanced periodontal disease, probe depth is greater than 6 millimeters.

As used herein, "periodontal disease" refers to a loss of supporting tissues of the teeth.

Figure 3:
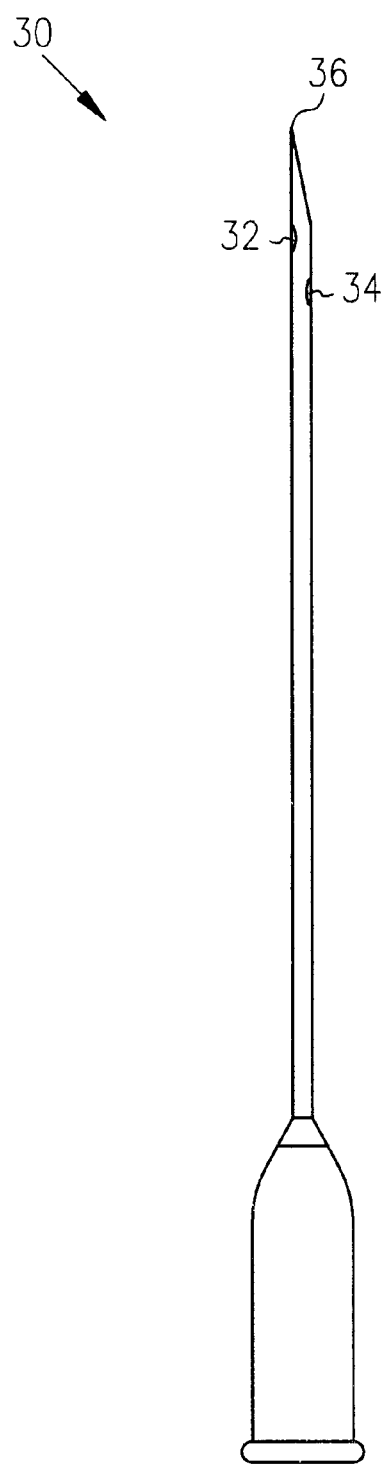
FIG. 3 is a top plan view of the needle of the present invention.
Figure 4:
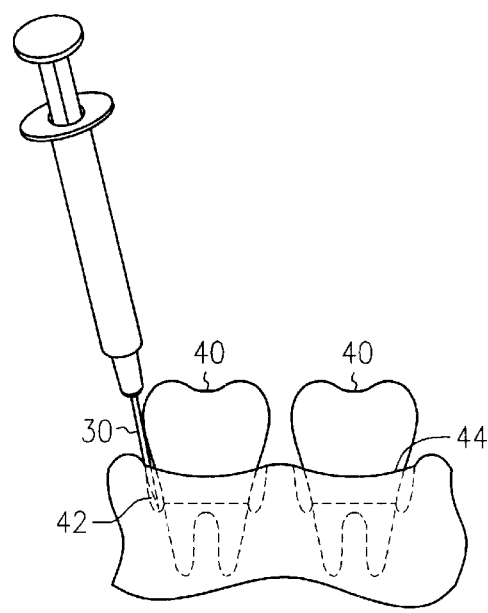
FIG. 4 is a side view of the diseased tooth, tooth pocket and position of the needle of the present invention.
Figure 4A:
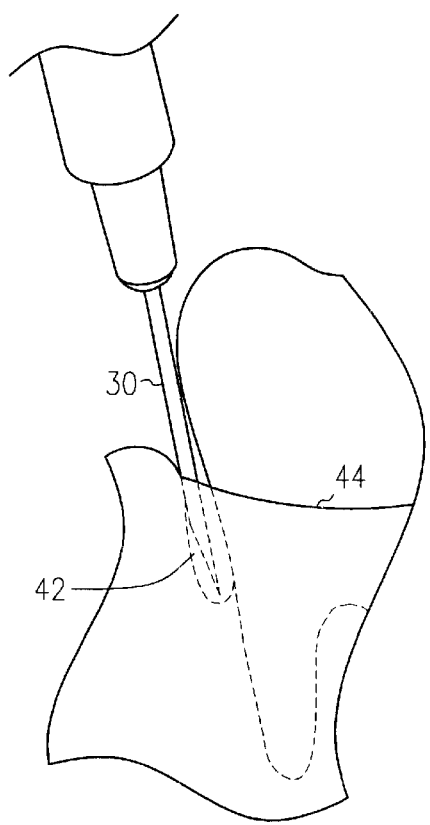
FIG. 4A is a side view of the needle in a periodontal pocket.
Figure 4B:
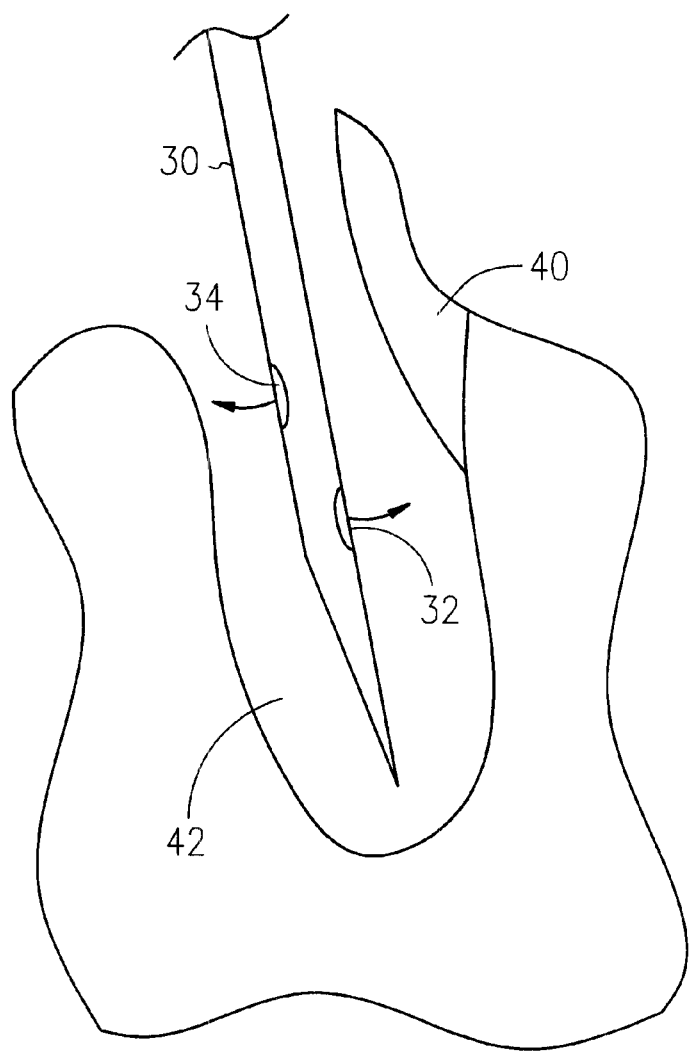
FIG. 4B is a side view of the needle with dual ports within the periodontal pocket.
Figure 5:
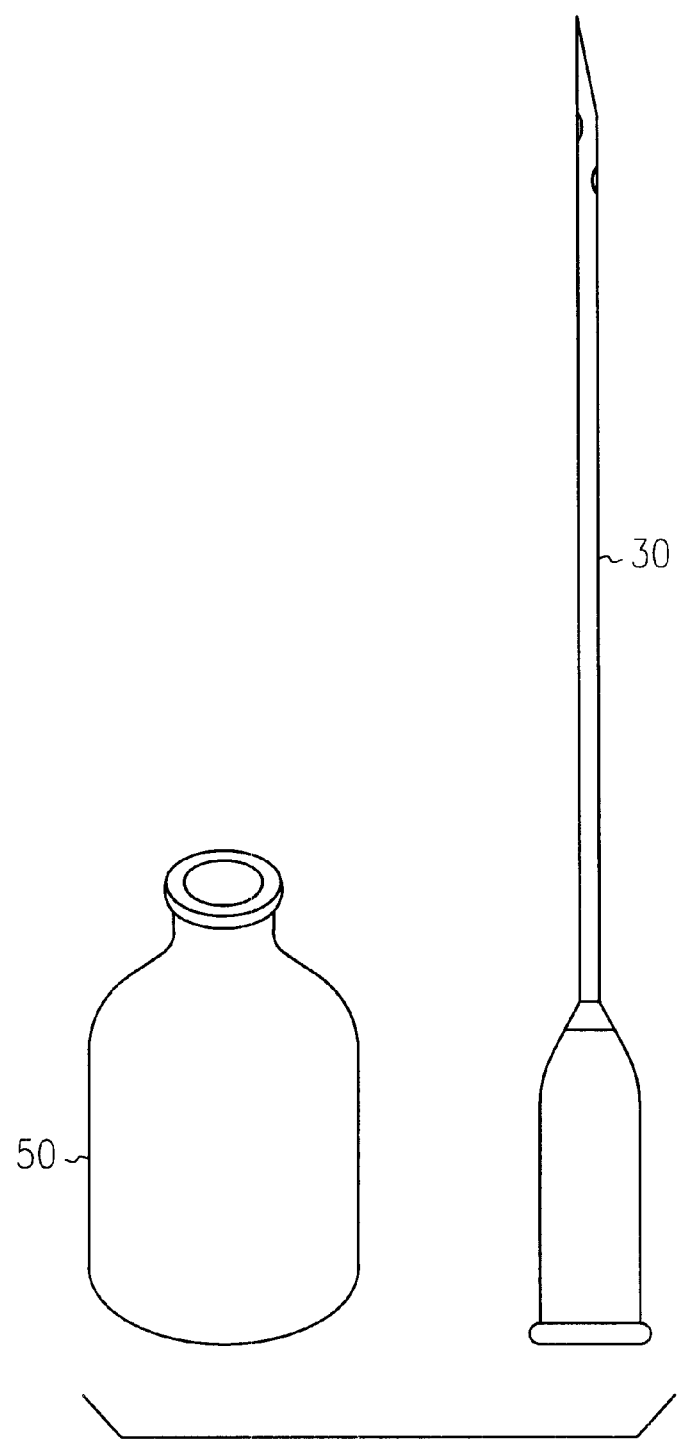
FIG. 5 is a perspective view of one kit embodiment.

One embodiment of the syringe needle of the present invention is illustrated at 30 in FIG. 3. The syringe needle 30 has a first port 32 and a second port 34 staggered with respect to the first port. The needle is made of a deformable material that permits the syringe needle to be positioned within the diseased pocket of a tooth. The syringe needle terminates in a tip 36. The sideholes 32 and 34 permit a more desirable flushing and introduction of fluids into the pocket. While a needle with two staggered ports is described herein, it is understood that a needle with a single port in usable in the method of the present invention. A needle with more than two ports is also usable for some method embodiments of the present invention.

The needle 30 is made from a material that permits reuse of the needle 30 and that is somewhat deformable. To be reused, the needle material must be autoclavable. Suitable needle materials include nitinol, stainless steel, and polymeric materials.

One other embodiment of the present invention includes a kit for treating periodontal disease. The kit comprises a container, the container 50 containing the viscous, reddish-brown sulfonated phenolic solution and a needle 30 for delivering the solution to a diseased pocket of a tooth. The kit also comprises, for some embodiments, a syringe and a container that contains sterile water. Each of the containers and the needle and the syringe, if present, is packaged in a larger container that encloses all of these items.

Although water is described herein as a rinse agent used in the method of the present invention, it is understood that aqueous solutions comprising additional components such as sodium carbonate, sodium citrate, sodium chloride and antibiotic components are also usable.

Since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes, which come within the meaning and range of equivalency of the claims, are intended to be embraced therein.

What is claimed is:

1. A method for treating periodontal disease, comprising:
   providing a device for delivering a reddish-brown solution comprising sulfuric acid and sulphonated phenolic compounds;
   delivering to a pocket of a tooth with periodontal disease, a viscous, reddish-brown solution comprising sulfuric acid and sulphonated phenolic compounds using the device; and
   retaining the reddish-brown solution in the pocket for a time ranging from about 5 seconds to about 60 seconds.

2. The method of claim 1 and further comprising pretreating the tooth by scraping and planing the tooth prior to delivering the reddish-brown solution.

3. The method of claim 1 and further comprising rinsing the pocket of the tooth with water or other aqueous solution prior to adding the reddish-brown solution.

4. The method of claim 1 and further comprising rinsing the pocket of the tooth with water or other aqueous solution after adding the reddish-brown solution.

5. The method of claim 1 and further comprising removing the reddish-brown solution by application of suction.

6. The method of claim 1 and further comprising providing a syringe needle for delivering the reddish-brown solution.

7. A method for saving condemned teeth, comprising:
   delivering to a pocket of condemned tooth, a viscous, reddish-brown solution comprising sulfuric acid and sulphonated phenolic compounds; and
   retaining the reddish-brown solution in the pocket for a time ranging from about 5 seconds to about 60 seconds.

8. The method of claim 7 further comprising rinsing the pocket of the condemned tooth with water or other aqueous solution prior to adding the reddish-brown solution.

9. The method of claim 7 and further comprising rinsing the pocket of the condemned tooth with water or other aqueous solution after adding the reddish-brown solution.

10. A kit comprising:
    a first container containing a viscous, reddish-brown sulfonated phenolic solution; and a syringe needle;
    a container for enclosing the first container and the syringe needle; and
    a second container for containing an aqueous rinse solution.

* * * * *